United States Patent [19]

Okabe et al.

[11] 4,308,258
[45] Dec. 29, 1981

[54] PYRIMIDIN-4-YL-PHOSPHORUS ESTERS AND INSECTICIDAL, ACARICIDAL OR NEMATOCIDAL COMPOSITIONS AND METHODS USING THEM

[75] Inventors: Takayuki Okabe, Nishinomiya; Kunio Mukai, Takarazuka; Masachika Hirano, Ibaraki, all of Japan

[73] Assignee: Sumitomo Chemical Company, Limited, Osaka, Japan

[21] Appl. No.: 114,737

[22] Filed: Jan. 24, 1980

[30] Foreign Application Priority Data

Feb. 5, 1979 [JP] Japan .................... 54-12497

[51] Int. Cl.$^3$ .................... A01N 57/16; A01N 57/32; C07F 9/65
[52] U.S. Cl. .................... 424/200; 544/243; 544/319
[58] Field of Search .................... 544/243; 424/200

[56] References Cited

U.S. PATENT DOCUMENTS

| | | | |
|---|---|---|---|
| 2,754,243 | 7/1956 | Gysin et al. | 424/200 |
| 3,159,630 | 12/1964 | Rigterink | 544/243 |
| 3,205,231 | 9/1965 | Fest | 544/243 |
| 4,168,304 | 9/1979 | Maurer et al. | 424/200 |

FOREIGN PATENT DOCUMENTS

| | | | |
|---|---|---|---|
| 641253 | 6/1964 | Belgium . | |
| 2747357 | 4/1979 | Fed. Rep. of Germany . | |
| 2804889 | 8/1979 | Fed. Rep. of Germany | 424/200 |
| 1436754 | 5/1976 | United Kingdom . | |

OTHER PUBLICATIONS

Schaeffer, et al., J. Org. Chem., 26, pp. 412–418 (1961).

*Primary Examiner*—Alton D. Rollins
*Assistant Examiner*—Diana G. Rivers
*Attorney, Agent, or Firm*—Stevens, Davis, Miller & Mosher

[57] ABSTRACT

Pyrimidin-4-yl-phosphorothionates of the formula (I),

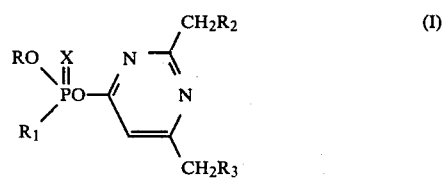

wherein R is a $C_1$–$C_2$ alkyl group, $R_1$ is a $C_1$–$C_2$ alkoxyl or $C_1$–$C_4$ alkylamino group, $R_2$ and $R_3$, which may be the same or different, are each a halogen atom, a $C_1$–$C_3$ alkoxyl or methylmercapto group, and X is an oxygen or sulfur atom; a process for producing pyrimidin-4-yl-phosphorothionates of the formula (I) characterized by condensing a 4-hydroxypyrimidine of the formula (II),

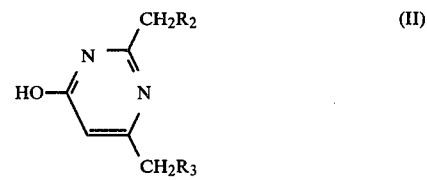

wherein $R_2$ and $R_3$, which may be the same or different, are each a halogen atom, a $C_1$–$C_3$ alkoxyl or methylmercapto group, with a halogen compound of the formula,

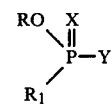

wherein R is a $C_1$–$C_2$ alkyl, $R_1$ is a $C_1$–$C_2$ alkoxyl or $C_1$–$C_4$ alkylamino group, Y is a halogen atom and X is an oxygen or sulfur atom; an insecticide, acaricide and nematocide characterized by containing pyrimidin-4-yl-phosphorothionates of the formula (I) as an active ingredient; 4-hydroxypyrimidines of the formula (II) wherein $R_2$ and $R_3$, which may be the same or different, are each a halogen atom, a $C_2$–$C_3$ alkoxyl or methylmercapto group; and a process for producing 4-hydroxypyrimidines of the formula (II) wherein $R_2$ and $R_3$, which may be the same or different, are each a halogen atom, a $C_2$–$C_3$ alkoxyl or methylmercapto group, characterized by reacting an acetamidine hydrochloride of the formula,

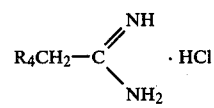

wherein $R_4$ is a halogen atom, a $C_2$–$C_3$ alkoxyl or methylmercapto group, with a β-ketoester of the formula,

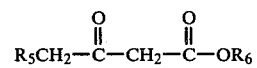

wherein $R_5$ is a halogen atom, a $C_2$–$C_3$ alkoxyl or methylmercapto group, and $R_6$ is a $C_1$–$C_2$ alkyl group.

10 Claims, No Drawings

PYRIMIDIN-4-YL-PHOSPHORUS ESTERS AND INSECTICIDAL, ACARICIDAL OR NEMATOCIDAL COMPOSITIONS AND METHODS USING THEM

The present invention relates to novel pyrimidin-4-yl-phosphorothionates, their production and insecticide, acaricide and nematocide compositions characterized by containing them as an active ingredient.

More particularly, the present invention relates to pyrimidin-4-yl-phosphorothionates of the formula (I),

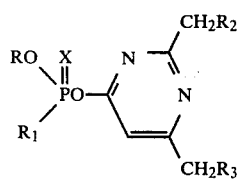

wherein R is a $C_1-C_2$ alkyl group, $R_1$ is a $C_1-C_2$ alkoxyl or $C_1-C_4$ alkylamino group, $R_2$ and $R_3$, which may be the same or different, are each a halogen atom, a $C_1-C_3$ alkoxyl or methylmercapto group, and X is an oxygen or sulfur atom.

Further, the present invention relates to a process for producing pyrimidin-4-yl-phosphorothionates of the foregoing formula (I) characterized by condensing a 4-hydroxypyrimidine of the formula (II),

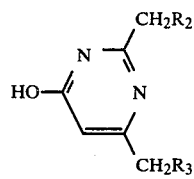

wherein $R_2$ and $R_3$ are as defined above, with a halogen compound of the formula (III),

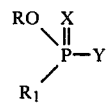

wherein R, $R_1$ and X are as defined above, and Y is a halogen atom. In the present invention, halogen atoms refer to chlorine and bromine atoms.

For example, when the starting materials of the formulae (II) and (III) are 4-hydroxy-2,6-bis(methoxymethyl)pyrimidine and O,O,-diethyl phosphorochloridothionate, respectively, condensation reaction between both materials proceeds according to the following equation:

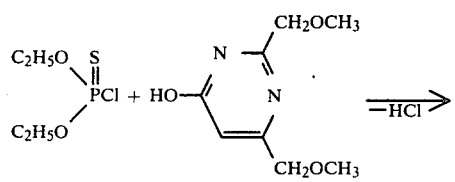
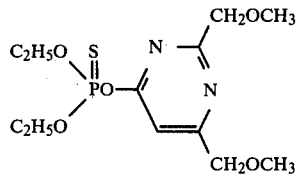

As the present compounds of the foregoing formula (I), the following compounds are for example given, but the present invention is not of course limited to these examples

| Number | Structure | Physical constant |
|---|---|---|
| (1) | $(CH_3O)_2P(S)$–O–[2-CH$_2$Cl, 6-CH$_2$Cl pyrimidin-4-yl] | $n_D^{19.0}$ 1.5440 |
| (2) | $(C_2H_5O)_2P(S)$–O–[2-CH$_2$Cl, 6-CH$_2$Cl pyrimidin-4-yl] | $n_D^{19.0}$ 1.5317 |
| (3) | $(CH_3O)_2P(S)$–O–[2-CH$_2$OCH$_3$, 6-CH$_2$OCH$_3$ pyrimidin-4-yl] | $n_D^{25.0}$ 1.5029 |
| (4) | $(C_2H_5O)_2P(S)$–O–[2-CH$_2$OCH$_3$, 6-CH$_2$OCH$_3$ pyrimidin-4-yl] | $n_D^{23.5}$ 1.4972 |
| (5) | $(CH_3O)_2P(S)$–O–[2-CH$_2$OC$_2$H$_5$, 6-CH$_2$OC$_2$H$_5$ pyrimidin-4-yl] | $n_D^{21.5}$ 1.5000 |
| (6) | $(C_2H_5O)_2P(S)$–O–[2-CH$_2$OC$_2$H$_5$, 6-CH$_2$OC$_2$H$_5$ pyrimidin-4-yl] | $n_D^{21.5}$ 1.4934 |
| (7) | $(CH_3O)_2P(S)$–O–[2-CH$_2$OC$_3$H$_7$(n), 6-CH$_2$OC$_3$H$_7$(n) pyrimidin-4-yl] | $n_D^{22.5}$ 1.4991 |

| Number | Structure | Physical constant | Number | Structure | Physical constant |
|---|---|---|---|---|---|
| (8) | (C2H5O)2P(S)-O-pyrimidine with CH2OC3H7(n), CH2OC3H7(n) | $n_D^{22.5}$ 1.4915 | (17) | (CH3O)2P(S)-O-pyrimidine with CH2OCH3, CH2Cl | $n_D^{23.0}$ 1.5285 |
| (9) | (CH3O)2P(S)-O-pyrimidine with CH2OC3H7(iso), CH2OC3H7(iso) | $n_D^{19.0}$ 1.4952 | (18) | (C2H5O)2P(S)-O-pyrimidine with CH2OCH3, CH2Cl | $n_D^{23.0}$ 1.5154 |
| (10) | (C2H5O)2P(S)-O-pyrimidine with CH2OC3H7(iso), CH2OC3H7(iso) | $n_D^{19.0}$ 1.4895 | (19) | (CH3O)2P(S)-O-pyrimidine with CH2OCH3, CH2OC2H5 | $n_D^{20.5}$ 1.5058 |
| (11) | (CH3O)2P(S)-O-pyrimidine with CH2SCH3, CH2SCH3 | $n_D^{20.5}$ 1.5719 | (20) | (C2H5O)2P(S)-O-pyrimidine with CH2OCH3, CH2OC2H5 | $n_D^{21.5}$ 1.4963 |
| (12) | (C2H5O)2P(S)-O-pyrimidine with CH2SCH3, CH2SCH3 | $n_D^{20.5}$ 1.5556 | (21) | (CH3O)2P(S)-O-pyrimidine with CH2OCH3, CH2SCH3 | $n_D^{20.0}$ 1.5433 |
| (13) | (CH3O)2P(O)-O-pyrimidine with CH2OCH3, CH2OCH3 | $n_D^{20.5}$ 1.4800 | (22) | (C2H5O)2P(S)-O-pyrimidine with CH2OCH3, CH2SCH3 | $n_D^{18.5}$ 1.5260 |
| (14) | (C2H5O)2P(O)-O-pyrimidine with CH2OCH3, CH2OCH3 | $n_D^{19.5}$ 1.4761 | (23) | (C2H5O)2P(S)-O-pyrimidine with CH2Cl, CH2OCH3 | $n_D^{23.0}$ 1.5146 |
| (15) | (CH3O)2P(O)-O-pyrimidine with CH2OC2H5, CH2OC2H5 | $n_D^{21.0}$ 1.4865 | (24) | (CH3O)2P(S)-O-pyrimidine with CH2Cl, CH2OC2H5 | $n_D^{22.5}$ 1.5261 |
| (16) | (C2H5O)2P(O)-O-pyrimidine with CH2OC2H5, CH2OC2H5 | $n_D^{19.5}$ 1.4743 | (25) | (C2H5O)2P(S)-O-pyrimidine with CH2Cl, CH2OC2H5 | $n_D^{22.5}$ 1.5115 |

| Number | Structure | Physical constant |
|---|---|---|
| (26) | (CH₃O)(CH₃O)P(=S)−O−C(=CH−C(CH₂OCH₃)=N−)−N=C−CH₂OC₂H₅ | $n_D^{27.0}$ 1.5034 |
| (27) | (C₂H₅O)(C₂H₅O)P(=S)−O−C(=CH−C(CH₂OCH₃)=N−)−N=C−CH₂OC₂H₅ | $n_D^{27.0}$ 1.4950 |
| (28) | (CH₃O)(CH₃O)P(=S)−O−C(=CH−C(CH₂OCH₃)=N−)−N=C−CH₂OC₃H₇(n) | $n_D^{28.5}$ 1.4993 |
| (29) | (C₂H₅O)(C₂H₅O)P(=S)−O−C(=CH−C(CH₂OCH₃)=N−)−N=C−CH₂OC₃H₇(n) | $n_D^{28.5}$ 1.4918 |
| (30) | (CH₃O)(CH₃O)P(=S)−O−C(=CH−C(CH₂OCH₃)=N−)−N=C−CH₂OC₃H₇(iso) | $n_D^{28.5}$ 1.4981 |
| (31) | (C₂H₅O)(C₂H₅O)P(=S)−O−C(=CH−C(CH₂OCH₃)=N−)−N=C−CH₂OC₃H₇(iso) | $n_D^{28.5}$ 1.4910 |
| (32) | (CH₃O)(CH₃O)P(=S)−O−C(=CH−C(CH₂OCH₃)=N−)−N=C−CH₂SCH₃ | $n_D^{26.0}$ 1.5381 |
| (33) | (C₂H₅O)(C₂H₅O)P(=S)−O−C(=CH−C(CH₂OCH₃)=N−)−N=C−CH₂SCH₃ | $n_D^{26.0}$ 1.5230 |
| (34) | (C₂H₅O)(C₂H₅O)P(=S)−O−C(=CH−C(CH₂OCH₃)=N−)−N=C−CH₂OC₂H₅ | $n_D^{28.5}$ 1.4710 |
| (35) | (CH₃NH)(CH₃O)P(=S)−O−C(=CH−C(CH₂OCH₃)=N−)−N=C−CH₂OCH₃ | $n_D^{25.0}$ 1.5282 |
| (36) | (C₂H₅NH)(CH₃O)P(=S)−O−C(=CH−C(CH₂OCH₃)=N−)−N=C−CH₂OCH₃ | $n_D^{21.0}$ 1.5222 |
| (37) | (n-C₃H₇NH)(CH₃O)P(=S)−O−C(=CH−C(CH₂OCH₃)=N−)−N=C−CH₂OCH₃ | $n_D^{24.0}$ 1.5192 |
| (38) | (iso-C₃H₇NH)(CH₃O)P(=S)−O−C(=CH−C(CH₂OCH₃)=N−)−N=C−CH₂OCH₃ | $n_D^{24.0}$ 1.5181 |
| (39) | (n-C₄H₉NH)(CH₃O)P(=S)−O−C(=CH−C(CH₂OCH₃)=N−)−N=C−CH₂OCH₃ | $n_D^{23.0}$ 1.5143 |
| (40) | (iso-C₄H₉NH)(CH₃O)P(=S)−O−C(=CH−C(CH₂OCH₃)=N−)−N=C−CH₂OCH₃ | $n_D^{23.0}$ 1.5160 |
| (41) | (sec-C₄H₉NH)(CH₃O)P(=S)−O−C(=CH−C(CH₂OCH₃)=N−)−N=C−CH₂OCH₃ | $n_D^{23.0}$ 1.5154 |
| (42) | (CH₃NH)(C₂H₅O)P(=S)−O−C(=CH−C(CH₂OCH₃)=N−)−N=C−CH₂OCH₃ | $n_D^{21.5}$ 1.5223 |
| (43) | (C₂H₅NH)(C₂H₅O)P(=S)−O−C(=CH−C(CH₂OCH₃)=N−)−N=C−CH₂OCH₃ | $n_D^{25.0}$ 1.5170 |

| Number | Structure | Physical constant |
|---|---|---|
| (44) | n-C₃H₇NH, C₂H₅O, P(=S)-O-[vinyl]-pyrimidine with CH₂OCH₃ (2-position) and CH₂OCH₃ (other) | $n_D^{25.0}$ 1.5150 |
| (45) | iso-C₃H₇NH, C₂H₅O, P(=S)-O-pyrimidine, CH₂OCH₃, CH₂OCH₃ | $n_D^{21.5}$ 1.4 |
| (46) | n-C₄H₉NH, C₂H₅O, P(=S)-O-pyrimidine, CH₂OCH₃, CH₂OCH₃ | $n_D^{23.0}$ 1.5118 |
| (47) | iso-C₄H₉NH, C₂H₅O, P(=S)-O-pyrimidine, CH₂OCH₃, CH₂OCH₃ | $n_D^{24.5}$ 1.5102 |
| (48) | sec-C₄H₉NH, C₂H₅O, P(=S)-O-pyrimidine, CH₂OCH₃, CH₂OCH₃ | $n_D^{25.0}$ 1.5106 |
| (49) | CH₃NH, CH₃O, P(=S)-O-pyrimidine, CH₂OCH₃, CH₂OC₂H₅ | $n_D^{21.3}$ 1.5212 |
| (50) | C₂H₅NH, CH₃O, P(=S)-O-pyrimidine, CH₂OCH₃, CH₂OC₂H₅ | $n_D^{21.3}$ 1.5166 |
| (51) | CH₃NH, C₂H₅O, P(=S)-O-pyrimidine, CH₂OCH₃, CH₂OC₂H₅ | $n_D^{21.3}$ 1.5160 |
| (52) | C₂H₅NH, C₂H₅O, P(=S)-O-pyrimidine, CH₂OCH₃, CH₂OC₂H₅ | $n_D^{21.3}$ 1.5110 |
| (53) | CH₃NH, CH₃O, P(=S)-O-pyrimidine, CH₂OCH₃, CH₂OC₃H₇(n) | $n_D^{20.5}$ 1.5201 |
| (54) | CH₃NH, C₂H₅O, P(=S)-O-pyrimidine, CH₂OCH₃, CH₂OC₃H₇(n) | $n_D^{20.5}$ 1.5158 |
| (55) | C₂H₅NH, H₃CO, P(=S)-O-pyrimidine, CH₂OC₂H₅, CH₂OC₂H₅ | $n_D^{25.5}$ 1.5106 |
| (56) | CH₃NH, C₂H₅O, P(=S)-O-pyrimidine, CH₂OC₂H₅, CH₂OC₂H₅ | $n_D^{25.5}$ 1.5100 |
| (57) | CH₃NH, CH₃O, P(=S)-O-pyrimidine, CH₂OCH₃, CH₂SCH₃ | $n_D^{20.0}$ 1.5600 |
| (58) | C₂H₅NH, CH₃O, P(=S)-O-pyrimidine, CH₂OCH₃, CH₂SCH₃ | $n_D^{18.0}$ 1.5531 |
| (59) | CH₃NH, C₂H₅O, P(=S)-O-pyrimidine, CH₂OCH₃, CH₂SCH₃ | $n_D^{17.5}$ 1.5507 |
| (60) | C₂H₅NH, C₂H₅O, P(=S)-O-pyrimidine, CH₂OCH₃, CH₂SCH₃ | $n_D^{22.0}$ 1.5441 |
| (61) | CH₃NH, CH₃O, P(=S)-O-pyrimidine, CH₂SCH₃, CH₂SCH₃ | $n_D^{21.0}$ 1.5815 |

-continued

| Number | Structure | Physical constant |
|---|---|---|
| (62) | C2H5NH, CH3O, PO, S, N=, CH2SCH3, N, CH2SCH3 | $n_D^{21.5}$ 1.5771 |
| (63) | CH3NH, C2H5O, PO, S, N=, CH2SCH3, N, CH2SCH3 | $n_D^{20.5}$ 1.5716 |
| (64) | C2H5NH, C2H5O, PO, S, N=, CH2SCH3, N, CH2SCH3 | $n_D^{23.0}$ 1.5691 |
| (65) | CH3NH, CH3O, PO, S, N=, CH2OCH3, N, CH2Cl | $n_D^{24.5}$ 1.5470 |
| (66) | C2H5NH, CH3O, PO, S, N=, CH2OCH3, N, CH2Cl | $n_D^{24.5}$ 1.5395 |
| (67) | CH3NH, C2H5O, PO, S, N=, CH2OCH3, N, CH2Cl | $n_D^{24.5}$ 1.5383 |
| (68) | C2H5NH, C2H5O, PO, S, N=, CH2OCH3, N, CH2Cl | $n_D^{24.5}$ 1.5324 |
| (69) | CH3NH, CH3O, PO, S, N=, CH2Cl, N, CH2Cl | $n_D^{21.0}$ 1.5620 |
| (70) | C2H5NH, CH3O, PO, S, N=, CH2Cl, N, CH2Cl | $n_D^{25.0}$ 1.5502 |
| (71) | CH3NH, C2H5O, PO, S, N=, CH2Cl, N, CH2Cl | $n_D^{21.0}$ 1.5518 |
| (72) | C2H5NH, C2H5O, PO, S, N=, CH2Cl, N, CH2Cl | $n_D^{22.0}$ 1.5431 |
| (73) | CH3NH, CH3O, PO, O, N=, CH2OCH3, N, CH2OCH3 | $n_D^{20.5}$ 1.5427 |
| (74) | C2H5NH, CH3O, PO, O, N=, CH2OCH3, N, CH2OCH3 | $n_D^{22.0}$ 1.5396 |
| (75) | CH3NH, C2H5O, PO, O, N=, CH2OCH3, N, CH2OCH3 | $n_D^{21.0}$ 1.5332 |
| (76) | C2H5NH, C2H5O, PO, O, N=, CH2OCH3, N, CH2OCH3 | $n_D^{21.0}$ 1.5314 |

The compounds of the present invention can be obtained with satisfactory results by reacting a 4-hydroxypyrimidine (II) with a halogen compound (III) in an amount of 0.9 to 1.2 time by mole based on the 4-hydroxypyrimidine at a temperature between about 0° C. and about 100° C. for one to several hours with stirring in a solvent in the presence of an inorganic salt or organic base and if necessary 0.1 to 10 mole % of copper powder, cuprous chloride or a phase transfer catalyst (e.g. quaternary ammonium salts, phosphonium salts, crown ether). The solvent includes for example ketones (e.g. acetone, methyl isobutyl ketone), acetonitrile, benzene, toluene and water. The inorganic salt includes for example anhydrous potassium carbonate and anhydrous sodium carbonate, and the organic base includes for example triethylamine and pyridine. After completion of the reaction, the objective compounds can be isolated by the common after-treatments, and if necessary they may further be purified, for example, by distillation or column chromatography on silica gel. As the phase transfer catalyst used herein, there may be given for example benzyltriethylammonium chloride, benzyltri-n-butylammonium chloride, tetra-n-butylammonium bromide, tri-n-octylmethylammonium chloride, 1,4,7,10,13,16-hexaoxacyclooctadecane, 1,4,7,10-tetraoxacyclododecane and benzyltriphenylphosphonium chloride.

4-Hydroxypyrimidines of the formula (II), starting materials for the present compounds, are produced by a method characterized by reacting an acetamidine hydrochloride of the formula (IV),

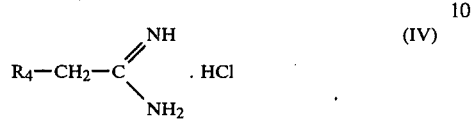

wherein $R_4$ is a halogen atom, a $C_1$–$C_3$ alkoxyl or methylmercapto group, with a β-ketoester of the formula (V),

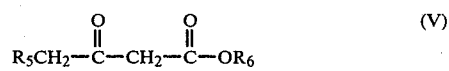

wherein $R_5$ is a halogen atom, a $C_1$–$C_3$ alkoxy or methylmercapto group, and $R_6$ is a $C_1$–$C_2$ alkyl group.

Referring now more particularly to the method, the objective pyrimidines can be obtained as crystals in a high yield as follows: A mixture of a β-ketoester (V) (1 mole) and an acetamidine hydrochloride (IV) (1 to 1.5 moles) is dissolved in an alcohol (e.g. methanol, ethanol), water or a mixture thereof, and a 10 to 30% aqueous solution of sodium alcoholate (e.g. sodium methylate, sodium ethylate) or alkali hydroxide (e.g. sodium hydroxide, potassium hydroxide), the amount of the solution being 2 to 2.5 times by mole based on acetamidine hydrochloride (IV), is added thereto at 5° to 30° C. with stirring; the reaction mixture is stirred at 10° to 50° C. for 1 to 10 hours and concentrated under reduced pressure; the resulting dark brown solid residue is dissolved in water in an amount of 2 to 5 times by volume (v/v) based thereon and the aqueous solution is adjusted to a pH of 4 to 6.5 with 6N hydrochloric acid at 5° to 10° C., followed by extraction with chloroform, methylene chloride or methyl isobutyl ketone; and the organic layer is dried over anhydrous sodium sulfate and concentrated under reduced pressure to obtain the objective pyrimidines.

The pyrimidines thus obtained have a sufficient purity to use without further purification, but they may be recrystallized to pure products from suitable solvents. Acetamidine hydrochlorides used as a starting material are obtained according to F. C. Schaefer et. al., J. Org. Chem., 26, 412 (1961).

Some specific examples of 4-hydroxypyrimidines of the formula (II),

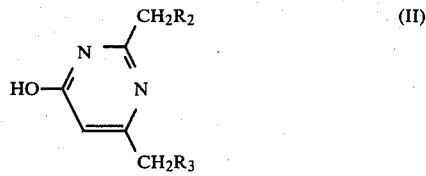

obtained by the method of the present invention will be given hereinafter.

| $R_2$ | $R_3$ | Melting point (°C.) |
|---|---|---|
| Cl | Cl | 136–138 |
| Cl | $CH_3O$ | 153–155 |
| $CH_3O$ | Cl | 124–125.5 |
| $CH_3O$ | $CH_3O$ | 96–97 |
| $CH_3O$ | $C_2H_5O$ | 96.5–98 |
| $CH_3O$ | $CH_3S$ | 68–70 |
| $C_2H_5O$ | $CH_3O$ | 93–95 |
| $i$-$C_3H_7O$ | $CH_3O$ | 49.5–51.5 |
| $i$-$C_3H_7O$ | $CH_3O$ | 70–72 |
| $CH_3S$ | $CH_3O$ | 153–155 |
| $C_2H_5O$ | $C_2H_5O$ | 69–71 |
| $n$-$C_3H_7O$ | $n$-$C_3H_7O$ | 91–94 |
| $i$-$C_3H_7O$ | $i$-$C_3H_7O$ | 80.5–82.0 |
| $CH_3S$ | $CH_3S$ | 101–102 |

Of 4-hydroxypyrimidines represented by the formula (II), only the one in which both $R_2$ and $R_3$ are a methoxy group is well known, and therefore the others are novel.

Some specific examples of the halogen compound, another starting material for the present compounds, will be given hereinafter.

O,O-Dimethyl phosphorochloridothionate
O,O-Diethyl phosphorochloridothionate
O,O-Di-n-propyl phosphorochloridothionate
O,O-Di-isopropyl phosphorochloridothionate
O,O-Dimethyl phosphorochloridate
O,O-Diethyl phosphorochloridate
O,O-Di-n-propyl phosphorochloridate
O,O-Di-isopropyl phosphorochloridate
O-Methyl N-methylphosphoramidochloridothionate
O-Methyl N-ethylphosphoramidochloridothionate
O-Methyl N-n-propylphosphoramidochloridothionate
O-Methyl N-isopropylphosphoramidochloridothionate
O-Methyl N-n-butylphosphoramidochloridothionate
O-Methyl N-isobutylphosphoramidochloridothionate
O-Methyl N-sec-butylphosphoramidochloridothionate
O-Methyl N-allylphosphoramidochloridothionate
O-Methyl N-cyanoethylphosphoramidochloridothionate
O-Ethyl N-methylphosphoramidochloridothionate
O-Ethyl N-ethylphosphoramidochloridothionate
O-Ethyl N-n-propylphosphoramidochloridothionate
O-Ethyl N-isopropylphosphoramidochloridothionate
O-Ethyl N-n-butylphosphoramidochloridothionate
O-Ethyl N-isobutylphosphoramidochloridothionate
O-Ethyl N-sec-butylphosphoramidochloridothionate
Corresponding phosphoramidochloridates The foregoing halogen compounds were synthesized according to the following literatures:

K. Sasse, Organische Phosphorverbindungen, in Methoden der Organischen Chemie, Vol XII/1, Müller, Ed., Georg Thieme Verlag, Stuttgart, 1963

K. Sasse, Organische Phosphorverbindungen, in Methoden der Organischen Chemie, Vol XII/2, Müller, Ed., Georg Thieme Verlag, Stuttgart, 1964

Still further, the present invention relates to an insecticide, acaricide and nematocide composition characterized by containing pyrimidin-4-yl-phosphorothionates of the formula (I),

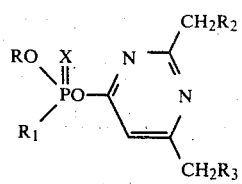

(I)

wherein R, $R_1$, $R_2$, $R_3$ and X are as defined above, as an active ingredient.

Insecticides, acaricides and nematocides have made a great contribution to remarkable increase in agricultural production through their controlling effects against various harmful insects parasitic on agricultural crops. However, various problems such as toxicity to mammals and pollution of natural environment have appeared and developed to such a degree that the use of these effective insecticides, acaricides and nematocides is feared in some fields.

For the reasons as described above, there is a strong demand for the development of insecticides, acaricides and nematocides which are low in toxicity, free from fear of environmental pollution and effective in controlling various harmful insects.

As a result of an extensive study to develop excellent insecticides, acaricides and nematocides satisfying the above requirements, the inventors found that the present compounds of the formula (I) have properties meeting the above requirements, and thus completed the present invention. The combined insecticide, acaricide and nematocide of the present invention are particularly suitable for controlling stem-borers, planthoppers, leafhoppers and bugs in paddy field; insects doing damage to vegetables, fruit trees and wood, for example insects belonging to Lepidoptera [e.g. diamondback moth (*Plutella xylostella*), armyworms and cutworms, tortorixes] and insects belonging to Orthoptera (e.g. grasshoppers); mites, nematodes, and disease-carrying mosquitoes, flies, cockroaches, ticks, fleas and lice; and insects harmful to stored cereals.

In the practical application of the present compounds, they may be applied alone without other components or in mixtures with carriers for ease of use as controlling agents. The commonly used preparation forms, for example emulsifiable concentrates, wettable powders, dusts, granules, fine granules, heating fumigants, aerosols and baits, can be produced optionally, with no need of particular conditions like common agricultural chemicals, by the methods wells known to those skilled in the art. The compounds of the present invention can be applied to various usages in required preparation forms and with required carriers.

Further, multi-purpose compositions of excellent efficacy can be produced by mixing with other active ingredients, for example, organo-phosphate insecticides such as O,O-dimethyl O-(3-methyl-4-nitrophenyl)phosphorothioate (hereinafter referred to as Fenitrothion) and O,O-dimethyl O-(2,2-dichlorovinyl)phosphate (hereinafter referred to as DDVP); carbamate series insecticides such as 1-naphthyl N-methylcarbamate, 3,4-dimethylphenyl N-methylcarbamate and 3,5-dimethylphenyl N-methylcarbamate; pyrethroid series insecticides such as Allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as resmethrin) and α-cyano-3-phenoxybenzyl 2-(4-chlorophenyl)isovalerate (hereinafter referred to as Fenvalerate); other insecticides, microbial pesticides such as fungicides, nematocides, acaricides, herbicides and B.T.; insect hormone compounds, other agricultural chemicals and fertilizers.

The preparations described above contain 0.1 to 95% by weight of the active ingredient (including other active ingredienets mixed) in general.

The present invention will be illustrated in more detail with reference to the following examples and preparation examples.

EXAMPLE 1 (Compound No. 4)

2,6-Bis(methoxymethyl)-4-hydroxypyrimidine (1.84 g, 0.01 mole) and anhydrous potassium carbonate (1.38 g, 0.01 mole) were suspended in acetone (50 ml), and refluxed for 15 minutes with stirring. After cooling to 35° C., O,O-diethyl phosphorochloridothionate (1.90 g. 0.01 mole) was added dropwise thereto, and the mixture was refluxed for 2 hours with stirring. After cooling to room temperature, the precipitate was filtered, and the filtrate was poured into toluene (200 ml). The toluene solution was washed with 5% aqueous sodium hydroxide solution, 5% aqueous hydrochloric acid and then water. The toluene layer was dried over anhydrous sodium sulfate and concentrated under reduced pressure to obtain 2.6 g of a yellow oily product. The product was further purified by column chromatography on silica gel to obtain 2.1 g of O,O-diethyl O-[2,6-bis(methoxymethyl)pyrimidin-4-yl]-phosphorothionate as a pale yellow oil (refractive index $n_D^{23.5}$ 1.4972).

| Elementary analysis: | C (%) | H (%) | N (%) |
|---|---|---|---|
| Calculated (as $C_{12}H_{21}N_2O_5PS$) | 42.86 | 6.25 | 8.33 |
| Found | 42.84 | 6.31 | 8.18 |

EXAMPLE 2 (Compound No. 42)

4-Hydroxy-2,6-bis(methoxymethyl)pyrimidine (1.84 g, 0.01 mole ) and anhydrous potassium carbonate (1.38 g, 0.01 mole) were suspended in acetone (30 ml), and refluxed for 30 minutes with stirring. After cooling to 35° C., O-ethyl N-methylphosphoramidochloridothionate (1.60 g, 0.01 mole) was added dropwise thereto, and the mixture was refluxed for 2 hours with stirring. After cooling the reaction mixture to room temperature, the precipitate was filtered, and the filtrate was poured into toluene (200 ml). The toluene solution was washed with 2.5% aqueous sodium hydroxide solution and then with water. The toluene layer was dried over anhydrous sodium sulfate and concentrated under reduced pressure to obtain 2.48 g of a pale brown oily residue. The residue was purified by column chromatography on silica gel to obtain 2.05 g of O-ethyl O-[2,6-bis-(methoxymethyl)pyrimidin-4-yl] N-methylphosphoramidothionate as a colorless oil (refractive index $n_D^{25.0}$ 1.5282).

The compounds, Nos. (1) to (3), (5) to (41) and (43) to (76), were synthesized in the same manner as above.

4-Hydroxypyrimidines of the formula (II) used as a starting material were produced, for example, by the following methods.

EXAMPLE 3

2,6-Bis(chloromethyl)-4-hydroxypyrimidine

Sodium methylate (5.4 g, 0.01 mole) was added to a solution of chloroacetamidine hydrochloride (6.45 g, 0.05 mole) and ethyl 4-chloroacetoacetate (8.3 g, 0.05 mole) in methanol (30 ml) at room temperature with stirring. The mixture was stirred at room temperature for 6 hours and concentrated under reduced pressure. The residue obtained was dissolved in water (50 ml).

The pH of this aqueous solution was adjusted to 4 to 5 with conc. hydrochloric acid, followed by extraction with chloroform. The chloroform extract was washed with water, dried over anhydrous sodium sulfate and concentrated under reduced pressure to obtain 6.8 g of a yellow residue.

The residue was recrystallized from ether to obtain 6.0 g of 2,6-bis(chloromethyl)-4-hydroxypyrimidine as colorless needle-like crystals (m.p. 136°–138° C.)

| Elementary analysis: | C (%) | H (%) | N (%) |
|---|---|---|---|
| Calculated (as $C_6H_{10}Cl_2N_2O$) | 37.30 | 3.11 | 14.51 |
| Found | 37.40 | 3.12 | 14.80 |

EXAMPLE 4

2,6-Bis(methylthiomethyl)-4-hydroxypyrimidine

To a solution of 2,6-bis(chloromethyl)-4-hydroxypyrimidine (3.86 g, 0.02 mole) in methanol (20 ml) was added dropwise 15% aqueous sodium methylmercaptane solution (11.20 g, 0.024 mole) with stirring. This solution was allowed to stand at room temperature for 2 days, poured into water (150 ml) and extracted with chloroform. The chloroform extract was washed with water, dried over anhydrous sodium sulfate and concentrated under reduced pressure to obtain 3.5 g of a yellow crystal. The crystal was recrystallized from ether to obtain 3.1 g of 2,6-bis(methylthiomethyl)-4-hydroxypyrimidine as colorless granular crystals (m.p. 101°–102° C.).

| Elementary analysis: | C (%) | H (%) | N (%) |
|---|---|---|---|
| Calculated (as $C_8H_{12}N_2OS_2$) | 44.44 | 5.56 | 12.96 |
| Found | 44.38 | 5.47 | 13.12 |

EXAMPLE 5

6-(Chloromethyl)-4-hydroxy-2-(methoxymethyl)-pyrimidine

Sodium methylate (11.90 g, 0.22 mole) was added to a solution of methoxyacetamidine hydrochloride (12.45 g, 0.1 mole) and ethyl 4-chloroacetoacetate (16.50 g, 0.1 mole) in methanol (50 ml) at 5° to 10° C. with stirring. The resulting orange reaction mixture was stirred at 5° to 10° C. for 2 hours and then at 20° C. for 3 hours, and neutralized with conc. hydrochloric acid. The precipitate was filtered, and the filtrate was concentrated under reduced pressure to obtain a residue which was then dissolved in water (300 ml). The aqueous solution was extracted with chloroform, and the chloroform extract was dried over anhydrous sodium sulfate, and concentrated under reduced pressure to obtain a crystalline residue. The residue was suspended in ether and then filtered to obtain 17.8 g of 6-(chloromethyl)-4-hydroxy-2-(methoxymethyl)pyrimidine as pale brown needle-like crystals (m.p. 124.0°–125.5° C.).

| Elementary analysis: | C (%) | H (%) | N (%) |
|---|---|---|---|
| Calculated (as $C_7H_9ClN_2O_2$) | 44.56 | 4.77 | 14.85 |
| Found | 44.50 | 4.79 | 14.92 |

EXAMPLE 6

4-Hydroxy-2-(methoxymethyl)-6-(methylthiomethyl)-pyrimidine 6-(Chloromethyl)-4-hydroxy-2-(methoxymethyl)-pyrimidine (3.8 g, 0.02 mole) was added to 10 ml of a 15% aqueous solution of sodium methylmercaptane at room temperature. After allowing to stand overnight, the resulting brown reaction solution was extracted with chloroform. The chloroform extract was dried over anhydrous sodium sulfate and concentrated under reduced pressure to obtain 3.9 g of a brown crystal. The crystal was recrystallized from n-hexane/benzene to obtain 2.8 g of 4-hydroxy-2-(methoxymethyl)-6-(methylthiomethyl)pyrimidine as white needle-like crystals (m.p. 68°–70° C.).

| Elementary analysis: | C (%) | H (%) | N (%) |
|---|---|---|---|
| Calculated (as $C_8H_{12}N_2O_2S$) | 47.98 | 6.04 | 13.99 |
| Found | 47.89 | 6.09 | 14.15 |

EXAMPLE 7

6-(Ethoxymethyl)-4-hydroxy-2-(methoxymethyl)-pyrimidine

Sodium methylate (6.5 g, 0.12 mole) was added to a solution of methoxyacetamidine hydrochloride (6.23 g, 0.05 mole) and ethyl ethoxyacetoacetate (8.72 g, 0.05 mole) in methanol (50 ml) at room temperature, and the resulting white suspension liquor was stirred at 45° to 50° C. for 4 hours. The reaction mixture was treated in the same manner as in Example 5. Recrystallization from ether gave 8.5 g of 6-(ethoxymethyl)-4-hydroxy-2-(methoxymethyl)pyrimidine as white needle-like crystals (m.p. 96.5°–98° C.).

Reference Example 1

2,6-Bis(methoxymethyl)-4-hydroxypyrimidine 2,6-Bis(chloromethyl)-4-hydroxypyrimidine (3.86 g, 0.02 mole) was mixed with a solution of sodium methylate (2.40 g, 0.044 mole) in methanol (50 ml), followed by refluxing for 3 hours with stirring.

The precipitate was filtered, and the filtrate was concentrated under reduced pressure to obtain a residue which was then dissolved in water (100 ml). The pH of this aqueous solution was adjusted to 4 to 5 with conc. hydrochloric acid, followed by extraction with chloroform. The chloroform extract was washed with water, dried over anhydrous sodium sulfate and concentrated under reduced pressure to obtain 3.1 g of a yellow crystal.

The crystal was recrystallized from ether to obtain 2.7 g of 2,6-bis(methoxymethyl)-4-hydroxypyrimidine as white needle-like crystals (m.p. 96°–97° C.).

| Elementary analysis: | C (%) | H (%) | N (%) |
|---|---|---|---|
| Calculated | 52.17 | 6.52 | 15.22 |

| Elementary analysis: | C (%) | H (%) | N (%) |
|---|---|---|---|
| (as $C_8H_{12}N_2O_3$) | | | |
| Found | 52.11 | 6.58 | 15.34 |

Reference Example 2

2,6-Bis(methoxymethyl)-4-hydroxypyrimidine

Sodium methylate (13.5 g, 0.25 mole) was added to a solution of chloroacetamidine hydrochloride (7.74 g, 0.06 mole) and ethyl 4-chloroacetoacetate (9.88 g, 0.06 mole) in methanol (100 ml) with stirring at a temperature between 10° C. and 15° C. The mixture was stirred for 1 hour at 25° C. and then refluxed for 3 hours with stirring. After the reaction mixture was cooled to room temperature, the precipitate was filtered, and the filtrate was treated in the same manner as in Reference Example 1 to obtain 6.6 g of 2,6-bis(methoxymethyl)-4-hydroxypyrimidine.

Reference Example 3

Methoxyacetamidine hydrochloride

Sodium methylate (1.62 g, 0.03 mole) was added all at once to a solution of methoxyacetonitrile (21.3 g, 0.3 mole) in methanol (100 ml) at room temperature with stirring, and the mixture was stirred at room temperature for 1 hour. Thereafter, ammonium chloride (16.1 g, 0.3 mole) was added all at once to the reaction solution, and after stirring at 35° to 40° C. for 2 hours, the reaction mixture was filtered. The filtrate was concentrated under reduced pressure to obtain a colorless, transparent oily product. The product was suspended in acetone, and the suspension was rapidly cooled to obtain 33.5 g of methoxyacetamidine hydrochloride as white crystals (m.p. 44°–45° C.).

| Elementary analysis: | C (%) | H (%) | N (%) |
|---|---|---|---|
| Calculated (as $C_3H_9ClN_2O$) | 28.92 | 7.23 | 11.24 |
| Found | 28.71 | 7.28 | 11.45 |

Preparation Example 1

Fifty parts of each of the present compounds (1) to (76) are dissolved in 40 parts of xylene, and 10 parts of Sorpol SM-200, an emulsifier, (a registered trademark of Toho Kagaku Co., a mixture of anionic surface active agent and a nonionic one) are added thereto. The mixture is thoroughly stirred to obtain an emulsifiable concentrate of each compound.

Preparation Example 2

Twenty parts of Fenitrothion (described above) are added to 20 parts of each of the present compounds (3), (4), (5), (35), (36), (37), (39) and (44), and then 50 parts of xylene and 10 parts of Sorpol SM-200 (described above) are added thereto. The mixture is thoroughly stirred to obtain an emulsifiable concentrate of each compound.

Preparation Example 3

Forty parts of each of the present compounds (1) to (76) are well mixed with 5 parts of Sorpol SM-200 (described above), and 55 parts of 300-mesh diatomaceous earth are added thereto. The mixture is well mixed while being stirred in a mortar to obtain a wettable powder of each compound.

Preparation Example 4

Eighty parts of each of the present compounds (1) to (76) are dissolved in 10 parts of xylene, and 10 parts of Sorpol SM-200, an emulsifier, (a registered trade mark of Toho Kagaku Co., a mixture of an anionic surface active agent and a nonionic one) are added thereto. The mixture is thoroughly stirred to obtain an emulsifiable concentrate of each compound.

Preparation Example 5

Three parts of each of the present compounds (1) to (76) are dissolved in 20 parts of acetone, and 97 parts of 300-mesh talc are added thereto. The mixture is thoroughly mixed while being stirred in a mortar, and acetone is then removed by evaporation to obtain a dust of each compound.

Preparation Example 6

Two parts of 3-methylphenyl N-methylcarbamate are added to 2 parts of each of the present compounds (6), (7), (8), (9), (40), (41), (42) and (43), and the mixture is dissolved in 20 parts of acetone. After adding 96 parts of 300-mesh talc thereto, the mixture is treated in the same manner as in Preparation Example 4 to obtain a dust of each compound.

Preparation Example 7

To 3 parts of each of the present compounds (1) to (76) are added 5 parts of Toyolignin CT (a salt of ligno-sulfonic acid, a registered trade mark of Toyo Spinning Co.) and 92 parts of GSM Clay (a registered trade mark of Zieklite Mining Co.), and the mixture is well mixed while being stirred in a mortar. Thereafter, the mixture is well mixed with water in an amount of 10% based thereon, granulated by means of a granulator and air dried to obtain a granule of each compound,.

Preparation Example 8

To 3 parts of each of the present compounds (1) to (76) are added 5 parts of Toyolignin CT (described above) and 92 parts of GSM Clay (described above), and the mixture is well mixed while being stirred in a mortar. Thereafter, the mixture is well mixed with water in an amount of 10% based thereon, granulated by means of a granulator for fine granule production and air dried to obtain a fine granule of each compound.

Preparation Example 9

0.2 Part of each of the present compounds (1) to (76) is dissolved in kerosene and made up to 100 parts with kerosene to obtain an oil spray of each compound.

Preparation Example 10

0.1 Part of tetramethrin is added to 0.2 part of each of the present compounds (3) and (35), and the mixture is made up to 100 parts with kerosene to obtain an oil spray of each compound.

Preparation Example 11

0.2 Part of each of the present compounds (14) and (42), 0.2 part of (+)-trans-Allethrin, 7 parts of xylene and 7.6 parts of deodorized kerosene are well mixed to make a solution. The solution is filled in an aerosol container. After attaching a valve portion to the container, 85 parts of a propellant (liquefied petroleum gas)

is charged therein under pressure through the valve to obtain an aerosol of each compound.

Preparation Example 12

0.2 Part of each of the present compounds (5) and (36), 0.1 part of tetramethrin, 11.7 parts of deodorized kerosene and 1 part of Atmos 300, an emulsifier, (a registered trade mark of Atlas Chemical Co., monoglyceride series emulsifier) are mixed. The mixture is then emulsified with addition of 50 parts of pure water. The emulsion is then filled in an aerosol container together with 37 parts of a 3:1 mixture of deodorized butane and deodorized propane to obtain a water-base aerosol of each compound.

EXAMPLE 8

The emulsifiable concentrate obtained in Preparation Example 1 was diluted 1000 times with water (corresponding to 500 ppm of the active ingredient). On the bottom of a polyethylene cup of 5.5 cm in diameter was placed a piece of filter paper of the same size, and 0.7 ml of the above dilute liquor was dropped on the filter paper. Sucrose (30 mg) was placed on the paper as bait. Thereafter, 10 housefly female adults (*Musca domestica*) were liberated in the cup which was then covered with a lid. After 48 hours, the dead and alive were counted to obtain mortality (2 replications).

| Test compound | Mortality (%) | Test compound | Mortality (%) | Test compound | Mortality (%) |
|---|---|---|---|---|---|
| (1) | 100 | (14) | 100 | (27) | 100 |
| (2) | 100 | (15) | 100 | (28) | 100 |
| (3) | 100 | (16) | 100 | (29) | 100 |
| (4) | 100 | (17) | 100 | (30) | 100 |
| (5) | 100 | (18) | 100 | (31) | 100 |
| (6) | 100 | (19) | 100 | (32) | 100 |
| (7) | 100 | (20) | 100 | (33) | 100 |
| (8) | 100 | (21) | 100 | (34) | 100 |
| (9) | 100 | (22) | 100 | (35) | 100 |
| (10) | 100 | (23) | 100 | (36) | 100 |
| (11) | 100 | (24) | 100 | (37) | 100 |
| (12) | 100 | (25) | 100 | (38) | 100 |
| (13) | 100 | (26) | 100 | (39) | 100 |
| (40) | 100 | (53) | 100 | (66) | 100 |
| (41) | 100 | (54) | 100 | (67) | 100 |
| (42) | 100 | (55) | 100 | (68) | 100 |
| (43) | 100 | (56) | 100 | (69) | 100 |
| (44) | 100 | (57) | 100 | (70) | 100 |
| (45) | 100 | (58) | 100 | (71) | 100 |
| (46) | 100 | (59) | 100 | (72) | 100 |
| (47) | 100 | (60) | 100 | (73) | 100 |
| (48) | 100 | (61) | 100 | (74) | 100 |
| (49) | 100 | (62) | 100 | (75) | 100 |
| (50) | 100 | (63) | 100 | (76) | 100 |
| (51) | 100 | (64) | 100 | (77) | 100 |
| (52) | 100 | (65) | 100 | (78) | 100 |
| | | | | No treatment | 0 |

EXAMPLE 9

The emulsifiable concentrates obtained in Preparation Example 1 were diluted 1000 times with water. The dilute liquor was sprayed on rice plants cultivated in a Wagner's pot at a rate of 15 ml per pot. After air-drying, the pot was covered with a wire-screen cage, and 15 smaller brown planthopper adults (*Laodelphax striatellus*) were liberated therein. In order to examine the residual effect, another group of 15 smaller brown planthopper adults were liberated therein 5 days after spraying. The dead and alive of each group were counted 24 hours after the group was liberated in the cage. The mortality is shown in the following table.

| Test compound | Liberation on the spraying day | Liberation 5 days after spraying | Test compound | Liberation on the spraying day | Liberation 5 days after spraying |
|---|---|---|---|---|---|
| (3) | 100 | 77 | (48) | 100 | 100 |
| (4) | 100 | 100 | (49) | 100 | 100 |
| (5) | 100 | 100 | (50) | 100 | 100 |
| (6) | 100 | 90 | (51) | 100 | 100 |
| (7) | 100 | 97 | (52) | 100 | 100 |
| (12) | 100 | 92 | (55) | 100 | 100 |
| (20) | 100 | 100 | (56) | 100 | 100 |
| (27) | 100 | 100 | (57) | 100 | 100 |
| (35) | 100 | 100 | (58) | 100 | 100 |
| (36) | 100 | 100 | (59) | 100 | 100 |
| (37) | 100 | 97 | (60) | 100 | 100 |
| (38) | 100 | 100 | (61) | 100 | 93 |
| (39) | 100 | 100 | (63) | 100 | 100 |
| (40) | 100 | 100 | (64) | 100 | 93 |
| (41) | 100 | 100 | (67) | 100 | 87 |
| (42) | 100 | 100 | (71) | 100 | 90 |
| (43) | 100 | 100 | (A) | 100 | 80 |
| (44) | 100 | 100 | Diazinon | 100 | 73 |
| (45) | 100 | 100 | | | |
| (46) | 100 | 100 | MPMC | 100 | 50 |
| (47) | 100 | 100 | No treatment | 0 | 3 |

(A):

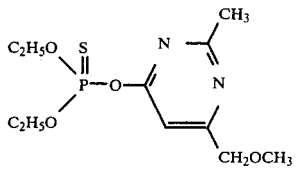

A compound disclosed in Published Unexamined Japanese Patent Application No. 95983/1978

Diazinon:

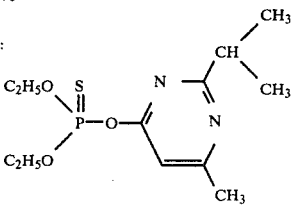

MPMC:

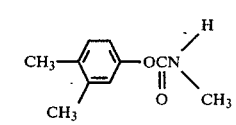

The controls were used as a 500 ppm solution.

EXAMPLE 10

The egg mass just before hatch of rice stem borer (*Chilo suppressalis*) was put on rice plants at the tillering stage cultivated in a 1/5000 Wagner's pot. After 3 days, granules containing the present compounds (3), (4), (5) and (6), respectively, among granules obtained in Preparation Example 7 were each applied thereto at a rate of 4 kg/10 are. Six days after application, the rice stem was cut to count the dead and alive of the larvae (2 replications). Water in the pot was maintained 3 cm deep throughout the test period.

| Test compound | Mortality (%) |
|---|---|
| (3) | 98 |

-continued

| Test compound | Mortality (%) |
|---|---|
| (4) | 100 |
| (5) | 92 |
| (6) | 95 |
| Diazinon* | 88 |
| No treatment | 8 |

*Control: 3% Granule was applied at a rate of 4 kg/10 are.

EXAMPLE 11

The egg mass just before hatch of rice stem borer (*Chilo suppressalis*) was put on rice plants cultivated in a 1/5000 Wagner's pot. After 4 days, granules containing the present compounds (35) and (45), respectively, among granules obtained in Preparation Example 7 were each applied thereto at a rate of 6 kg/10 are. As a control, a 3% granule of Diazinon was applied at a rate of 6 kg/10 are. Five days after application, the rice stem was cut to count the dead and alive of the larvae (2 replications). Water in the pot was maintained 3 cm deep throughout the test period.

| Test compound | Mortality (%) |
|---|---|
| (35) | 100 |
| (45) | 100 |
| Diazinon | 100 |
| No treatment | 4 |

EXAMPLE 12

Five milliliters of the oil spray obtained in Preparation Example 10 was sprayed on about 100 housefly adults (*Musca domestica*) per group, according to the Campbell's turn-table method [Soap and Sanitary Chemicals, Vol. 14, No. 6, 119 (1938)]. The housefly adults were exposed to the descending mist for 10 minutes. After 10 minutes, more than 80% of the houseflies could be knocked down, and the mortality after 24 hours was 100%.

EXAMPLE 13

Of the emulsifiable concentrates obtained in Preparation Example 1, those containing the present compounds (3), (4), (5), (6), (35), (45), (54) and (75), respectively, were each diluted 500 times with water. Ten milliliters of the dilute liquor was placed in a 20-ml beaker with a ground stopper, and then 0.5 ml of a liquor containing numerous nematodes (*Panagrellus redivivus*) was added thereto. After 48 hours, the dead and alive were examined by means of a binocular microscope, and it was found that all or most of the nematodes could be killed in each case.

EXAMPLE 14

The insecticidal activity on housefly adults (*Musca domestica*) of each aerosol obtained in Preparation Examples 11 and 12 was tested by the aerosol test method (Soap and Chemical Specialities, Blue Book, 1965) using a (6 ft)$^3$ Peet Grady's chamber. As a result, with any aerosol, more than 80% of the flies could be knocked down 15 minutes after spraying, and more than 70% of the flies could be killed by the next day.

EXAMPLE 15

Each dust obtained in Preparation Example 6 was applied, by means of a Bell jar duster, on potted rice seedlings (diameter of pot, 10 cm), which had elapsed 20 days after sowing, at a rate of 2 kg/10 are under a pressure of 200 mmHg. After application, the pot was covered with a wire-screen cage, and about 20 green rice leafhopper adults (*Nephotettix cincticeps*) were liberated therein. After 24 hours, the dead and alive were counted, and it was found that the mortality was 100% in each case.

EXAMPLE 16

Carmine mite female adults (*Tetranychus cinnabarinus*) were made parasitic on the leaves of potted kidney bean (primary leaf stage), at a rate of 10–15/leaf, which had elapsed 9 days after sowing, and bred at 27° C. for a week in a constant temperature room. Then, it was found that numerous carmine mites bred to various growth stages. At this time, a 1000-fold aqueous dilute liquor of each of the emulsifiable concentrates obtained in Preparation Example 1 was sprayed on the kidney bean at a rate of 10 ml/pot by means of a turn table. Eight days after spraying, the degree of damage of kidney bean and the number of female adults were examined (2 replications).

| Test compound | Degree of damage* | Number of female adults |
|---|---|---|
| (3) | — | 0 |
| (4) | — | 0 |
| (5) | — | 0 |
| (6) | — | 13 |
| (A) | − to + | 18 |
| Diazinon | − to + | 26 |
| Chlorodimeform | − to + | 25 |
| No treatment | +++ | 748 |

(A) Control: Described above.

| Test compound | Degree of damage* | Number of female adults |
|---|---|---|
| (35) | — | 0 |
| (36) | — | 0 |
| (37) | — | 1 |
| (38) | — | 0 |
| (39) | — | 0 |
| (40) | — | 0 |
| (41) | — | 2 |
| (42) | — | 0 |
| (44) | — | 0 |
| (45) | — | 0 |
| (46) | — | 0 |
| (47) | — | 0 |
| (48) | — | 8 |
| (53) | — | 11 |
| (59) | — | 5 |
| (65) | — | 0 |
| (73) | — | 13 |
| (76) | — | 0 |
| Chlorodimeform** | − to + | 19 |
| No treatment | +++ | 684 |

*The degree of damage was classified as follows:
− : <10%
++ : 50-90%
+ : 10-50%
+++ : >90%
**Control: Used as a 1000-fold dilute liquor of the 50% emulsifiable concentrate.

What is claimed is:

1. A pyrimidin-4-yl-phosphorothionate of the formula,

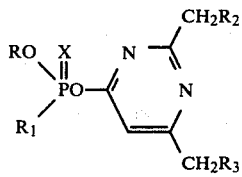

wherein R is a $C_1$–$C_2$ alkyl group, $R_1$ is a $C_1$–$C_2$ alkoxyl or $C_1$–$C_4$ alkylamino group, $R_2$ and $R_3$, which may be the same or different, are each a halogen atom or a $C_1$–$C_3$ alkoxyl or methylmercapto group, and X is an oxygen or sulfur atom.

2. The compound according to claim 1, wherein $R_1$ is a $C_1$–$C_2$ alkoxyl or $C_1$–$C_2$ alkylamino group and X is sulfur atom.

3. O,O-Diethyl O-[2,6-bis(methoxymethyl)pyrimidin-4-yl]phosphorothionate.

4. O,O-Dimethyl O-[2,6-bis(methoxymethyl)pyrimidin-4-yl]phosphorothionate.

5. O-Methyl O-[2,6-bis(methoxymethyl)pyrimidin-4-yl] N-methylphosphoramidothionate.

6. O-Methyl O-[2,6-bis(methoxymethyl)pyrimidin-4-yl] N-ethylphosphoramidothionate.

7. O-Ethyl O-[2,6-bis(methoxymethyl)pyrimidin-4-yl] N-methylphosphoramidothionate.

8. O-Ethyl O-[2,6-bis(methoxymethyl)pyrimidin-4-yl] N-ethylphosphoramidothionate.

9. An insecticidal, acaricidal or nematocidal composition comprising an inert carrier and as the active ingredient an insecticidally, acaricidally or nematocidally effective amount of a compound according to claim 1.

10. A method for controlling an insect, mite or nematode which comprises contacting the insect, mite or nematode with an insecticidally, acaricidally or nematocidally effective amount of a compound according to claim 1.

* * * * *